United States Patent [19]
Tovey

[11] Patent Number: 5,955,376
[45] Date of Patent: Sep. 21, 1999

[54] DETECTION OF MOLECULES ASSOCIATED WITH AIRBORNE PARTICLES

[75] Inventor: Euan R Tovey, Petersham, Australia

[73] Assignee: The University of Sydney, Sydney, Australia

[21] Appl. No.: 08/793,493

[22] PCT Filed: Aug. 25, 1995

[86] PCT No.: PCT/AU95/00539

§ 371 Date: Feb. 26, 1997

§ 102(e) Date: Feb. 26, 1997

[87] PCT Pub. No.: WO96/07099

PCT Pub. Date: Mar. 7, 1996

[30] Foreign Application Priority Data

Aug. 26, 1994 [AU] Australia ................................ PM 7658

[51] Int. Cl.[6] ................ G01N 33/558; G01N 33/563; G01N 21/00; G01N 33/53

[52] U.S. Cl. ................ 436/514; 422/58; 422/60; 422/101; 435/7.2; 435/7.21; 435/7.32; 435/34; 435/40.51; 436/513; 436/519; 436/523; 436/524; 436/177

[58] Field of Search ................ 422/58, 60, 101; 435/7.2, 7.21, 7.32, 34, 40.51; 436/513, 514, 519, 523, 524, 177

[56] References Cited

U.S. PATENT DOCUMENTS

| | | | |
|---|---|---|---|
| 4,948,561 | 8/1990 | Hinckley et al. | 422/61 |
| 5,091,318 | 2/1992 | Anawis et al. | 436/513 |
| 5,168,063 | 12/1992 | Doyle et al. | 435/240.27 |
| 5,328,851 | 7/1994 | Zaromb | 436/178 |
| 5,601,998 | 2/1997 | Mach et al. | 435/34 |
| 5,633,140 | 5/1997 | Wex et al. | 435/7.1 |

FOREIGN PATENT DOCUMENTS

| | | |
|---|---|---|
| WO 91/05260 | 4/1991 | WIPO. |
| WO 93/18404 | 9/1993 | WIPO. |

OTHER PUBLICATIONS

Jordan et al., "Aerosol–generated sol–gel–derived thin films as biosensing platforms," Analytica Chimica Acta, 332(1):83–91, Oct. 10, 1996.

Tovey et al., "Enhanced immunodetection of blotted house dust mite protein allergies . . . ," Chemical Abstracts, 110(21):190590c, May 22, 1989.

Schumacher, M.J. et al. "Recognition of pollen and other particulate . . . " Department of Pediatrics, College of Medicine, and the Respiratory Sciences Div., University of Arizona Health Sciences Center, Tucson, Ariz., pp. 608–616.

*Primary Examiner*—James C. Housel
*Assistant Examiner*—Gailene R. Gabel
*Attorney, Agent, or Firm*—Nixon & Vanderhye

[57] ABSTRACT

A method for detecting macromolecular species present on or in particles wherein particles are collected onto a surface, and the macromolecular species are allowed to diffuse from the particles. The diffused macromolecular species in close proximity to the particles are immobilized nonspecifically, wherein an immobilized macromolecular species is sufficiently close to a particle so as to be indicative of being diffused from the particle. The presence of the macromolecular species is detected while maintaining the close proximity of the immobilized macromolecular species to the particles from which the macromolecular species diffused.

26 Claims, 2 Drawing Sheets

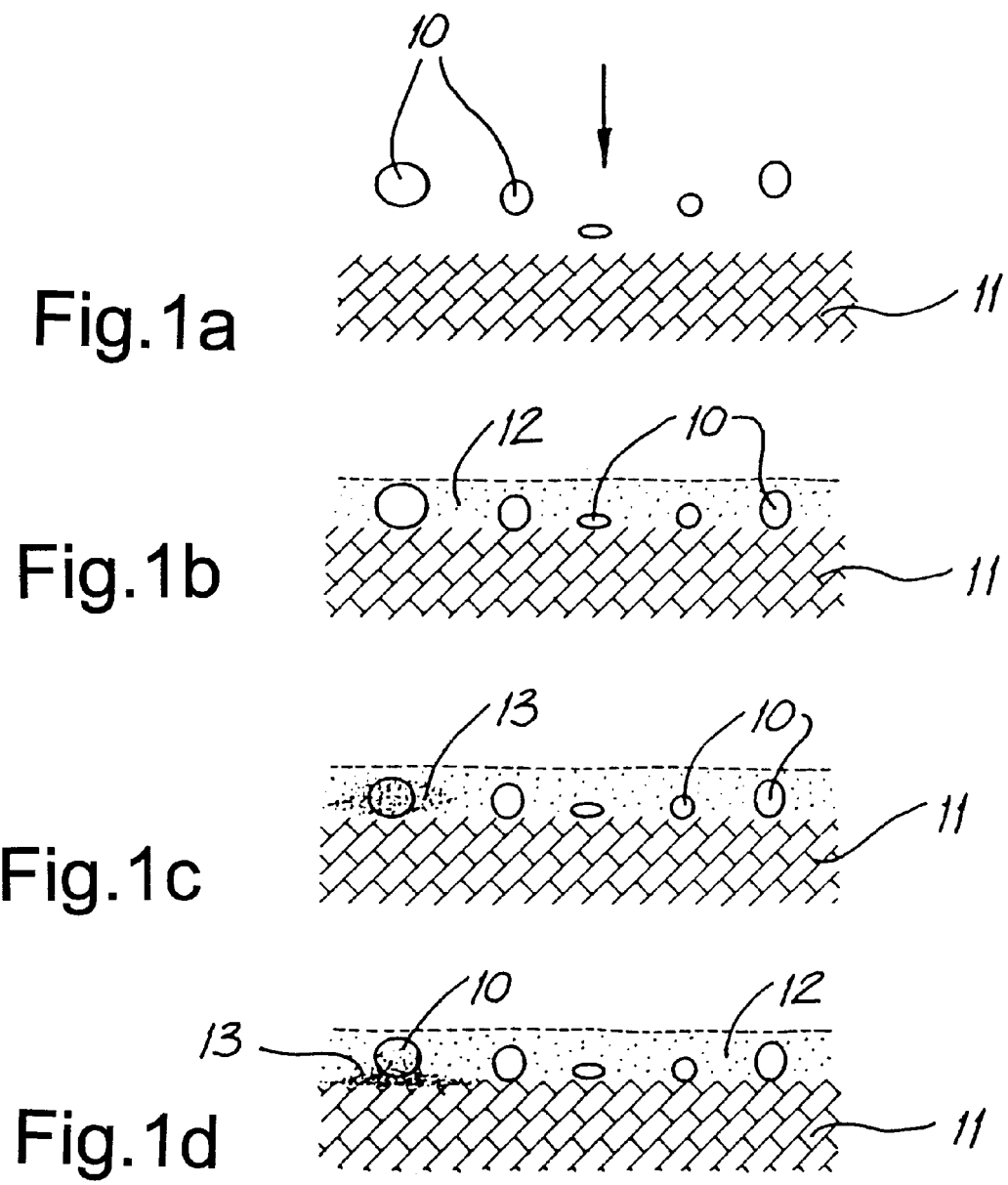

ര്5,955,376

DETECTION OF MOLECULES ASSOCIATED WITH AIRBORNE PARTICLES

BACKGROUND OF THE INVENTION

1. Field of the Invention

The present invention relates to a method for the detection and identification of macromolecules of interest associated with particles. More particularly the invention relies upon the diffusion of macromolecules from the particle, and their binding in proximity to the particle to enable the macromolecules to be identified as belonging to a particular class of particles. The method may also include the identification of the particles from which the macromolecules are diffused.

2. Description of Related Art

There are many situations in which particles in a fluid stream may cause disease, environmental damage or be of interest for some other reason. In some case, the fluid stream may be carrying a large number of different particles. In this case it may be difficult to determine which of the particles are causing the effect being studied. A particular example is that asthma is believed to be associated with airborne allergens. There may, however, be many airborne allergens in the air but only one or a few may be causing the asthma.

Asthma is a chronic disease affecting all age groups in the community. The study of asthma has been hindered by the shortage of suitable methods to identify and measure the characteristics of allergen exposure which is relevant to the disease. These characteristics include:

(1) the identify of the allergen;

(2) the quantity of the allergens; and (3) the size of the particles which are the allergen source.

It may be desired to know which of the particles present in the patient's environment are responsible for the observed symptoms. This may allow a determination of the source of the allergens and suggest mechanisms for prophylactically treating the condition.

It has long been conventional to estimate exposure to pollen allergens by collecting pollen particles on sticky surfaces, identifying them by morphological criteria and individually counting them. Mould exposure has been similarly monitored by biological and/or morphological methods. In each of these cases the identifiable biological particles are used as a proxy for the quality of allergens present in the sampled environment. These methods require highly skilled operators and are very labour intensive. They also suffer from the problem that the presence of a particular particle does not indicate that that particle is the source of the allergen of interest.

Immunoassays of allergens from many sources (pollens, mites, fungi, animal dander, etc.) based on aqueous extraction of material collected on filters and traps has the advantages of speed and simplicity if suitable specific antisera is available. These methods also allow quantification of the exposure to the specific allergens. There is, however, no one-to-one relationship established by such methods between specific allergens and individual particles, as the allergens are extracted from the entire sample of collected particles. There is thus no ability to associate a specific type of particle with sensitisation of the patient in a way commonly associated with an observed disease state.

The known methods of particle detection and analysis do not readily allow the provision of an answer to the most fundamental question about characterising allergen exposure i.e., "What aeroallergens are present that an individual is allergic to?". Skin-prick testing, RAST assays and questioning by a physician cannot definitely elucidate what allergens are producing the observed symptoms. In some cases, using such tests may be quite misleading as they cannot determine the time when an individual was exposed to the sensitising allergen nor can they detect sensitisation to allergens not in the test panel.

Not only is it important in a number of clinical situations to identify a specific offending allergen, it is also impossible in a more general sense to be able to make a cross sectional study of an exposure situation to understand the composition of different allergens which may be present. There are no methods which specifically focus on identifying allergen sources per se. This takes on added importance in an era when allergic disease is said to be increasing, yet we are unable to probe the environment to know if there are new, as yet unidentified, allergens present.

It has been shown in Tovey ER et al, Am. Rev. Resp. Dis. 1981; 124:630–635 that individual airborne mite faecal particles can be identified by a ring of immunoprecipitation developed around them following their impaction onto a bed of agarose containing allergen specific antibody. The identification of the particles was made by microscopy. Problems associated with this system are that only very short exposure times of the agarose bed is possible and that only specific polyclonal high-titre (hyper immune) antisera specific for a predetermined antigen can be used. Such high-titre sera is normally only available from an animal, such as a rabbit, that has been repeatedly injected with the allergen or antigen of interest and an adjuvant. The method would not work directly with IgE antibodies in the serum of an allergic person or with monoclonal antibodies. In neither of these cases is a visible immunoprecipitate formed.

The feasibility of using nitrocellulose membranes to press-blot antigens from individual particles has been described in Schumacker et al. J. Al. Clin.Imm. 1988; 82:608–16. In this method the particles collected and the nitrocellulose allergen blot are separated so that the immunostained antigens cannot be associated with the specific particles from which they originated.

SUMMARY OF THE INVENTION

The present invention consists in a method for the detection and identification of macromolecular species associated with particles, comprising the steps of:

a) collecting the particles onto a surface;

b) causing the macromolecular species, if present, to diffuse out of the particles;

c) immobilising non-specifically the diffused macromolecules in close proximity to the particles; and d) detecting the presence or absence of the macromolecules while maintaining the close proximity of the bound macromolecules, if any, and the particles from which they diffused.

The method according to this invention is particularly adapted for the identification of the source of an allergic reaction in a patient. Air in the vicinity of the patient may be sampled and particles entrained in the sampled air may be collected. After the antigens in those particles have diffused out of the particles and been bound in close proximity to the particles the patient's serum may be used to distinguish those antigens to which the patient is allergic from those to which he or she is not allergic. As the allergens are bound in proximity with the particles from which they are derived it is then possible to identify the particle visually or in some other way. In another aspect, the present invention consists in a method for the detection of macromolecules antigenic or allergenic to a patient and the identification of particles with which those macromolecules are associated, the method comprising the steps of a) collecting the particle onto a surface;

b) causing soluble macromolecules associated with the particles to diffuse out of the particles;

c) immobilising non-specifically at least some of the possibly antigenic or allergenic macromolecules that diffused out of the particles in close proximity to the particles;

d) detecting those immobilised macromolecules that are antigenic or allergenic to the patient; and e) identifying the particle associated with the macromolecules and from which the macromolecules diffused.

The invention, in preferred embodiments, exploits the discovery that many allergens occur naturally as highly soluble proteins concentrated within the particles that carry them. It has thus been found that while the total antigen exposure may be very small, the allergen concentration per particle, and thus per unit volume, is very high. This discovery allows detection of allergen carrying particles as the large number of allergen molecules diffusing from the particles may be readily visualised. The method can be used for other purposes including collecting bacteria, viruses or other particles of biological material from liquid streams such as water streams or air streams. It could also be used to characterise particles in exhaled air to assist in diagnosis of a disease state. After lysis of the bacteria or other particle, if necessary, to allow diffusion of detectable macromolecules the nature of the bacteria or other particles may be ascertained.

The particles will typically be less than 100 $\mu$ and often less than 20 $\mu$. The size of allergen bearing particles differs between allergen source and at different times from the same source. The clinical relevance is that particles larger than about 10 $\mu$ diameter have a much reduced chance of entering the lower respiratory tract and directly provoking acute symptoms. Cat allergens, for instance, can be associated with both large particles and small particles of typically less than 3 $\mu$ diameter, the latter being airborne substantially continuously. Mite allergens, by contrast, are mainly associated with faecal particles of from 7 to 40 $\mu$ diameter. In the case of Rye grass, allergens occur on large particles which are pollen grains and a small, "sub-micronic", particles which are starch granules released by the pollen.

As used in this specification the term "close proximity" means, in relation to the binding of the diffused macromolecules, that the binding is sufficiently close that there is a substantial possibility of uniquely associating a diffused macromolecule or a group of such macromolecules with a particular particle. The actual maximum distance will bear a relationship to the extent to which the particles are spaced apart over the surface; the capacity and avidity of the surface and/or any overlying layer to bind eluted material; the quantity of the macromolecules eluted from each particle and the sensitivity of the assay technique used for detecting the diffused macromolecules. In this last respect the concentration of the diffused macromolecules may be important to allow visualisation or other detection of the diffused macromoles. If the macromolecules are allowed to diffuse too far from their associated particle then their concentration may be too low to allow detection.

In preferred embodiments of the invention the diffusion and binding of the macromolecules results in the majority of the macromolecules being bound within 10 to 200 microns, and more preferably of from 50 to 100 microns, of the outer edge of a particle from which they originated, depending on the particle size and other considerations. In relative terms, this binding should occur within a distance of one to ten diameters of the particle, with more than 90% of the macromolecules binding within a radial distance equivalent to 5 diameters of the particle.

The macromolecular species released by the particles may be proteins, nucleic acids, glycoproteins, polysaccharides or other similar molecules. Typically the macromolecular species will be water soluble such that they may be caused to diffuse out of the particle merely by maintaining the surface on which the particle has been collected moist, or by rendering that surface moist in advances of the collection of the particles onto it. In other cases it may be necessary to lyse or otherwise treat the particle to release the macromolecular species. Any macromolecule which is capable of being diffused, or otherwise released, from a particle is regarded as being associated with that particle.

The particles may be collected onto the surface by filtration, impaction or by transfer from another surface on which they have been collected. The surface may itself be the surface onto which particles are impacted by entraining a fluid stream, such as a stream of air or water, into a jet. Particles in the fluid stream are, by virtue of their inertia, impacted against the surface while the fluid stream is diverted laterally. Filtration may be carried out using a suitable membrane, formed, for example, of nitrocellulose or a nucleopore membrane in which the pores are smaller than the particles.

If desired the surface may be coated with an adhesive substance to increase the retention of the particles on the surface and/or to aid in the preservation of required aspects of the biological activity of the particle or of the macromolecules.

The molecules diffused from the particles may be bound in proximity to the particles in any suitable manner. Soluble molecules may be eluted from the particles onto a membrane capable of binding the eluted material by one or more of the mechanisms of hydrophobic interactions, hydrophilic interactions, ionic interactions, van de Waals forces, electrostatic forces or covalent coupling. Nitrocellulose, nylon and polyvinylidine fluoride membranes may be used, for example, to bind proteins, glycoproteins and nucleic acids.

In one preferred embodiment of the invention particles are captured onto a membrane, such as nitrocellulose, that is capable of binding eluted proteins. The particles are then overlain with a thin layer of even thickness, for example, between 10 and 50 $\mu$m, of a buffered aqueous gel, (such as one of agarose or polyacrylamide), or a porous, aqueous, hydrophilic film. Such a layer or gel could provide a source of moisture to elute soluble proteins from the particles and would be of such a thickness that the proteins would largely diffuse parallel to the membrane and become bound in close proximity to the particle. The layer or film should have a porosity and nature to allow subsequent reactions to characterise and identify the particles. In an even more preferred embodiment a thin layer of an aqueous gel or hydrophilic film is applied to the surface prior to the collection of the particles and a second layer or film is applied after that collection.

In another preferred embodiment the particles are collected on a surface that will not itself bind the eluted molecules. In this case, the particles are overlain with a thin layer or film capable of binding the eluted molecules. There are numerous ways in which such a layer or film could bind the eluted molecules. One of these is by activation with protein binding groups.

If desired both the surface on which the particles are collected and the overlain layer or film may be able to bind to the eluted proteins or other molecules. In a still further embodiment of the invention neither the underlying surface nor the overlying layer or film has the capacity to bind the eluted molecules. In this case, a binding or cross-linking agent is used to localise the diffusing eluted molecules in the vicinity of the particles of their origin. In the case of proteins a suitable cross-linking agent may be gluteraldehyde.

It may also be possible to affix to the surface or to the layer or film applied thereto, ligands that will bind to the diffused macromolecules and hold them in close proximity to the particles. Such ligands could be antibodies, lectins or the like. The bound macromolecules would then be separately detected as has already been described.

A still further embodiment of the invention involves the application of a hydrated gel layer to the membrane that is then partially or fully dried prior to particle collection. In such a system the collection surface and/or the overlain gel layer may be protein binding or non-binding. In this case, after particles have been collected the gel layer would be re-hydrated so as to elute soluble molecules from the particles. The eluted molecules are bound by the collection surface, by the overlain gel layer or by added cross-linking reagents depending upon the nature of the system used. In each case the eluted molecules are bound in close proximity to the particles from which they were eluted. The outer surface of the dried overlain layer may be coated with an adhesive permeable to the diffused molecules and to the detection system but which assists in retaining the collected particles in place on the dried overlain layer.

In any of the foregoing cases the overlain layer or film may include substances which would enhance the elution or solubilisation of molecules and/or aid in their preservation and/or increase their immunogenicity. Such agents could include detergents, lysis agents or include detergents, lysis or precipitating agents such as polyvinyl pyrolidone. One could also add substances that increase the production of eluted antigens or other molecules characteristic of the particles. An example would be the addition of nutrients to cause fungae to excrete allergenic molecules, such as enzymes, or to excrete after molecules that may assist in characterising the fungae.

The substrate surface onto which the particles and/or the overlain layer or film are deposited in preferably itself a film or membrane. In this way, the collection and detection substrate is made easier to handle. Disks, strips or rolls of the substrate may be conveniently inserted into, and removed from, a particle collection device of any suitable design. They may also be conveniently handled during detection of the eluted molecules and identification of the particles.

Once the particles and eluted proteins are respectively located and immobilised in association with one another they are available for characterisation and identification.

The first step is to locate eluted molecular species of interest. This may be advantageously done using IgE from the subject of an allergic disease. The use of such antibodies will directly answer the fundamental question "what is present in the environment of the subject that is causing the allergic disease or symptoms?" Alternatively, the immobilised eluted molecules could be immunostained with a range of allergen-specific, or antigen-specific, or carbohydrate-specific probes, which could be antibodies or lectins respectively.

The localisation of a primary probe may be made with a secondary probe labelled with a reporter group, such as a fluorescent labelled antibodies against the primary probes.

Another reporter group could be an enzyme which produces an insoluble coloured product or reaction with a soluble substrate. If desired, in another embodiment of the invention, the primary probe could itself be labelled. A wide variety of known techniques are available for this purpose. Once the molecule of interest are labelled or otherwise identified it is then possible to characterise and identify the particles from which those molecules diffused. Such characterisation and identification may be done visually by origin or type specific staining or labelling of the particles themselves. If appropriately fluorescently labelled antibodies are used it would be possible to identify, for instance, whether any, and if so how many, particles from a particular source, e.g. cat dander, was associated with eluted molecules implicated in the disease or condition of interest.

The macromolecules may be detected in other ways. They may, for instance, undergo characteristic reactions that may be observed. An immobilised enzyme may, for instance, be detected with a chromogenic substrate.

The method according to this invention may be used to identify the source of a previously unknown allergen a person is allergic to; to provide a cross sectional view of the different airborne allergens/antigens present in an environment; or to monitor for the presence and or quantity of specific antigens or antigen sources including microbial material or particles of plant or animal origin.

Many other particulate materials could be characterised or identified and a more general purpose could be to gain a cross sectional view of all particles present which have an identifiable, detectable characteristic. Examples of such characteristics would be specific markers of a genus of bacteria or other micro organism or the presence of a specific antigen. The source of sampled material is not restricted to airborne material and could be applied to water-borne material.

A feature of the method is that soluble proteins are bound in a detectable or characterisable form in close proximity to the particles of their origin, so that the local concentration is high enough to be detected and the association between the particulate source and eluted protein is retained. Thus, the particles may contain molecules which, if eluted into free solution for a different system of assay, may be difficult to measure because their concentration would be too low. In addition the association between the particulate source and eluted protein would be lost.

BRIEF DESCRIPTION OF THE DRAWINGS

FIG. 1 shows diagrammatically four steps in a first embodiment of the method of particle detection and identification according to this invention.

DETAILED DESCRIPTION OF THE INVENTION

Figure 2A:
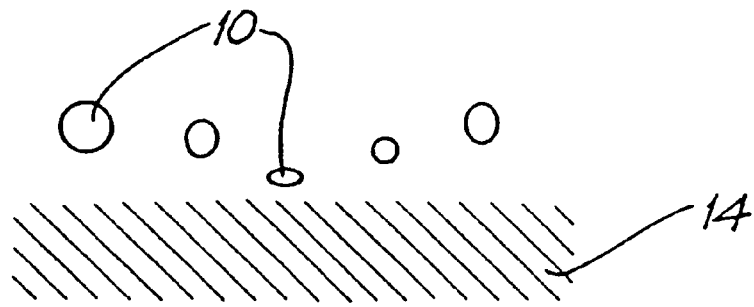
FIG. 2 show diagrammatically three steps in a second embodiment of the method of particle detection and identification according to this invention.

As is shown in FIG. 1(i) a variety of particles 10 are collected on the surface of a nitrocellulose membrane 11 able to bind and immobilise proteins. A layer of a porous hydrated gel or film 12 is then laid down on the membrane 11 retaining the particles 10 on the membrane 11 (FIG. 1(i)). Soluble molecules 13 present in the particles will be eluted therefrom by the water present in the hydrated gel or film (FIG. 1(iii)). Any soluble proteins 13 eluted from the particles will be bound to the membrane (FIG. 1(IV)). These molecules are thus immobilised in close association with the particles from which they were eluted and are available for any one of a large number of identifications procedures. As the molecules are bound in the membrane in close association with particles from which they eluted it is possible to positively identify not only the presence of the molecules of interest but also the particles from which they were derived.

Figure 2B:
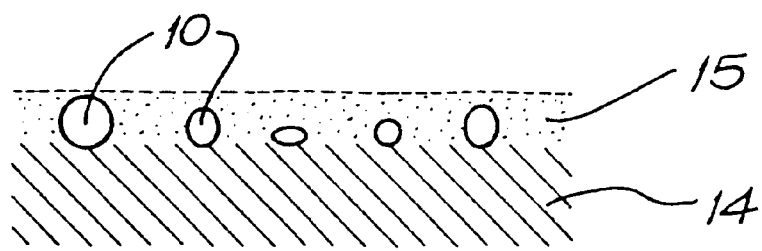
Figure 2C:
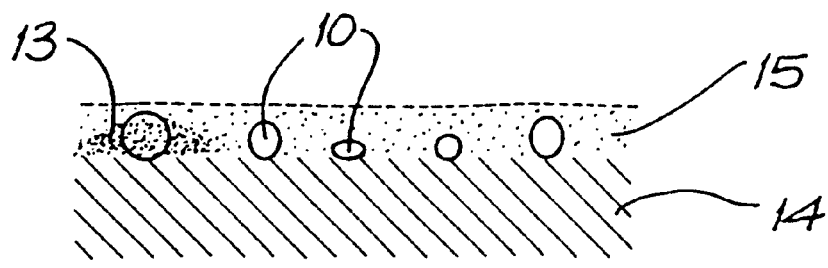

FIG. 2 shows an alternative embodiment of the invention. In this method the particles 10 are collected on a membrane 14 that is not protein binding (FIG. 2(i)). A hydrated protein binding film is then layed over the particles 10. Moisture in the film causes soluble proteins 13 to be eluted from the particles 10 and to be bound to the film 15. The molecules are thus immobilised and rendered available for identification and/or characterisation. The molecules 13 are again immobilised in close relationship with the particles from which was eluted. This facilitates determination of the source of the molecules of interest.

EXAMPLES

Sections (10×10 mm) of nitrocellulose membrane (0.22 $\mu$m pore size) are pre-coated with 0.3% agarose (in PBS (phosphate buffered saline)), using an ultrasonic nebuliser (FISONeb). The nebuliser is modified with a curved tube to direct its output downward and through a narrow slot (about 10×1 mm). The agarose temperature is approximately 50° C. The agarose aerosol is applied until a thin film of approximately 10 $\mu$m is established. Higher concentrations of agarose are possible, up to 3%. The use of aerosolised agarose gives a more stable bond between the film and the agarose than directly applying pre-formed sheets of agarose film.

The antigen source is then applied. For example, mite faecal particles or ryegrass pollen can be sprinkled or impacted onto the agarose layer. The film and particles are then stored in a humid container overnight in order to elute the soluble proteins from the particles and to allow these proteins to bind to the membrane. This binding is localised close to the particle.

A second, similar layer of 0.3% agarose film is then applied, as previously described. This layer may be thicker (~30 $\mu$ depth). It is important that the film is applied slowly so that the new layer does not form a liquid layer and so allow the particles to flow or that the particles are not disturbed from their initial positions.

Vacant protein-binding sites on the nitrocellulose are then blocked by incubating the coated film in a solution containing an irrelevant protein (skim milk powder, 3%) in PBS containing 0.02% TWEEN 20 (polyoxyethylene (20) sorbitan monostearate) (PBS/TWEEN) for 1 h at 37° C.

The blocked membrane is rinsed in PBS/TWEEN.

The antigens which are bound to the nitrocellulose are then detected with a primary antisera specific for that antigen. Sections of coated nitrocellulose piece are incubated with the primary antibody (anti-mite or anti-ryegrass antisera raised in rabbits), diluted 1:500. Anti-mite allergen Der p 1 or Der p 2 monoclonal antibodies (obtained from the University of Virginia) can also be used at a dilution 1 $\mu$/ml. If human atopic sera was to be used it would be applied at this point, but at a concentration of 1:2 to 1:10. Antibodies are diluted in 3% skim milk solution and incubated for 2 h at room temperature with gentle agitation. The membranes were then washed six times with agitation in 10 ml PBS/TWEEN, each wash lasting 5 minutes to remove unbound primary antibody.

The bound primary antibody is then detected by incubation with a labelled second antibody. For detection of primary rabbit antibody, sheep anti-rabbit immunoglobulin affinity isolated FITC conjugated antibodies, (Silenus Brand, catalogue number: RAF) are used at a dilution of 1:100 in 3% skim milk and PBS/TWEEN. For detection of human and mouse primary antibodies, second antibodies of appropriate specificity are used. Incubation is for at least 1 hour.

Membranes are then washed to remove unbound second antibody by incubation overnight in PBS/TWEEN followed by 5 lots of 5 minute washes with gentle agitation in PBS/TWEEN. Sections are then mounted on glass slides in 90% glycerol/10% PBS and viewed under a fluorescent microscope (Leitz Ortholux II).

In the case of pollens, the particles are observed to be surrounded by a ring of immunostaining on the nitrocellulose. Non-pollen particles are not stained.

I claim:

1. A method for determining the presence or amount of a macromolecular species on or in a particle, the method comprising the steps of:
   a) collecting the particle onto a porous surface such that the particle is attached to or retained on the surface, wherein the surface is not capable of supporting the growth or maintenance of a microorganism;
   b) allowing the macromolecular species to diffuse from the particle to the surface;
   c) non-specifically immobilizing the diffused macromolecular species to the surface within a distance of one to ten diameters of the particle so that the macromolecular species is sufficiently close to the particle so as to be identifiable as having diffused from that particle; and
   d) detecting a known physical or chemical characteristic of the diffused macromolecular species while maintaining the distance between the immobilized macromolecular species and the particle thereby detecting the presence or amount of the macromolecular species on or in the particle.

2. The method as claimed in claim 1 in which the surface is selected from the group consisting a membrane, a layer forming a film and a multilayer thereof.

3. The method as claimed in claim 2 in which the membrane is formed of a material selected from the group consisting of nitrocellulose, nylon, and polyvinylidene difluoride.

4. The method as claimed in claim 2 in which the layer forming a film is formed of a material selected from the group consisting of agarose, cellulose, polyvinyl alcohol, and polyacrylamide.

5. The method as claimed in claim 1 in which the surface binds the diffused macromolecular species non-specifically to effect the immobilization.

6. The method as claimed in claim 1 in which the macromolecular species is water soluble and is allowed to diffuse from the particles by rendering the particles moist after the collection step.

7. The method as claimed in claim 1, in which the particle is lysed after the collection step to allow the macromolecular species to diffuse therefrom.

8. The method as claimed in claim 1 which the the particle is an air-borne particle collected onto the surface by filtration or impaction.

9. The method as claimed in claim 1 in which the surface is coated with an adhesive substance which collects and retains the particle on the surface.

10. The method as claimed in claim 1 in which the particle is overlain with a layer, film or multilayer after being collected on the surface in order to ensure the particle is retained on the surface.

11. The method as claimed in claim 10 in which the layer, film or multilayer is hydrated after the particle is collected onto the porous surface thereby moistening the particle upon contact therewith sufficient to allow diffusion of the macromolecular species from the particle to the surface.

12. The method as claimed in claim 10 in which the layer, film or multilayer binds non-specifically the macromolecular species diffused from the particle to the surface.

13. The method as claimed in claim 10 in which the layer, film or multilayer is formed of a material selected from the group consisting of agarose, cellulose, polyvinyl alcohol, and polyacrylamide.

14. The method as claimed in claim 10 in which the layer, film or multilayer has an average thickness of from 10 to 50 μm.

15. The method as claimed in claim 10 in which neither the surface nor the layer, film or multilayer is capable of immobilizing the diffused macromolecular species and a cross-linking agent is applied to the outer surface of the layer, film or multilayer after the application of the layer, film or multilayer to the particle such that the cross-linking agent immobilizes non-specifically the diffused macromolecular species to the surface.

16. The method as claimed in claim 15 in which the cross-linking agent is glutaraldelyde.

17. The method as claimed in claim 10 in which the layer, film or multilayer further comprises one or more substances for solubilizing, precipitating, or dissolving macromolecular species.

18. The method as claimed in claim 1 in which a layer, film or multilayer of a hydratable material is used to form the surface before collecting the particle.

19. The method as claimed in claim 18 in which the macromolecular species is allowed to diffuse from the particle by hydrating the layer, film or multilayer after collecting the particle.

20. The method as claimed in claim 1 in which the physical or chemical characteristics of the macromolecular species is detected in situ in step (d) by one or more means selected from the group consisting of immunoreaction, enzyme reaction, visual inspection, microscopic inspection, labelling with a probe, tagging, and luminescence.

21. The method as claimed in claim 1 in which the macromolecular species is detected directly by contacting a detectably-labelled probe which binds specifically to the macromolecular species and detecting the presence of the probe bound to the macromolecular species by identifying the presence of the label on the surface, or detected indirectly by adding a first probe which binds specifically to the macromolecular species followed by contacting a second detectably-labelled probe which binds to the first probe bound to the macromolecular species and detecting the presence of the label on the surface.

22. The method as claimed in claim 21 in which the probe comprises IgE obtained from a subject.

23. The method as claimed in claim 1 further including the step of:

(e) identifying the particle from which the macromolecular species diffused.

24. The method as claimed in claim 23 in which the particle is identified by visual inspection.

25. The method as claimed in claim 24 in which the particle is identified by contacting a probe which binds specifically to the particle and detecting the presence of the probe bound to the particle.

26. A method of antigenic or allergenic macromolecular species present on or in particles and being antigenic or allergenic to a patient, and the identification of the particles which the macromolecular species are on or in, the method comprising the steps of:

(a) collecting the particles onto a porous surface such that the particles are attached to or retained on the surface, wherein the surface is not capable of supporting the growth or maintenance of a microorganism;

(b) allowing soluble macromolecular species to diffuse from the particles to the surface;

c) nonspecifically immobilizing the diffused antigenic and allergenic macromolecular species to the surface within a distance of one to ten diameters of the particles so that the macromolecular species is sufficiently close to the particles so as to be identifiable as having diffused from the particles; and d) detecting by immunological means the immobilized antigenic and allergenic macromolecular species while maintaining the distance between the immobilized macromolecular species and the particles thereby detecting the presence or amount of the macromolecular species on or in the particles; and e) identifing the particles from which the antigenic and allergenic macromolecular species diffused by contacting a probe which binds specifically to the particles and detecting the presence of the probe bound to the particles.

* * * * *